United States Patent [19]

Brossmer et al.

[11] Patent Number: 5,405,753
[45] Date of Patent: Apr. 11, 1995

[54] CMP-ACTIVATED, FLUORESCING SIALIC ACIDS, AS WELL AS PROCESSES FOR THEIR PREPARATION

[76] Inventors: Reinhard Brossmer, Kurt-Lindemann-Str. 21, D-6903 Neckargemünd; Hans J. Gross, Ringstrasse 5, D-6901 Dossenheim, both of Germany

[21] Appl. No.: 927,406
[22] PCT Filed: Mar. 19, 1991
[86] PCT No.: PCT/EP91/00530
    § 371 Date: Sep. 28, 1992
    § 102(e) Date: Sep. 28, 1992
[87] PCT Pub. No.: WO91/14697
    PCT Pub. Date: Oct. 3, 1991

[30] Foreign Application Priority Data

Mar. 26, 1990 [DE] Germany ............ 40 09 630.0

[51] Int. Cl.⁶ .................. C12Q 1/48; C12Q 1/00; G01N 33/566; C07G 3/00
[52] U.S. Cl. ............................. 435/15; 435/7.1; 435/815; 435/175; 436/501; 436/547; 436/548; 436/819; 536/4.1
[58] Field of Search .............. 435/15, 7.1, 815, 175, 435/4; 436/547, 548, 193, 819, 501; 536/4.1

[56] References Cited

U.S. PATENT DOCUMENTS

| | | | |
|---|---|---|---|
| 5,032,505 | 7/1991 | Pierce et al. | 435/193 |
| 5,059,535 | 10/1991 | Mazid et al. | 435/815 |
| 5,173,407 | 12/1992 | Uemura et al. | 436/548 |
| 5,180,674 | 1/1993 | Roth | 435/819 |

OTHER PUBLICATIONS

Gross et al, European Jour. of Biochem, vol. 177, No. 3 (1988).
Gross et al., "A Highly Sensitive Fluorometric Assay for Sialytransferase Activity Using CMP-9-flurore-sceinyl-NeuAc as Donor" Analytical Biochemistry, 186:127-134 (1990).
Gross et al., "Enzymatic Introduction of a Fluorescent Sialic Acid into Oligosaccharide Chains of Glycoproteins", Eurpoean Journal of Biochemistry, 177:583-89 (1988).
Chemical Abstracts, 77:(9) 57834u.
Chemical Abstracts, 109:(13) 108046C.

Primary Examiner—Michael G. Wityshyn
Assistant Examiner—Louise N. Leary
Attorney, Agent, or Firm—Foley & Lardner

[57] ABSTRACT

A process for preparing CMP-activated fluorescence indicator-labelled sialic acids is disclosed. According to the process, a 5-acylamido-9-amino-3,5,9-tridesoxy-β-D-glycero-D-galactonoulosonic acid or 5-aminoacylamido-3,5-didesoxy-β-D-glycero-D-galactonoulosonic acid is reacted with cytidine phosphate in the presence of a CMP-sialic acid synthase which is then reacted with a fluorescing compound to give a CMP-activated fluorescing sialic acid. Also disclosed are novel CMP-activated fluorescing sialic acids.

22 Claims, 2 Drawing Sheets

R =

(A)

(B)

CMP-ACTIVATED, FLUORESCING SIALIC ACIDS, AS WELL AS PROCESSES FOR THEIR PREPARATION

BACKGROUND OF THE INVENTION

The subject of the present invention is a new process for the preparation of CMP-activated (cytidine-5'-monophosphate), fluorescing or absorbing as well as new CMP-activated fluorescing or absorbing sialic acids.

Sialic acids (also called acylneuraminic acids) are components of many bacterial and animal glycoproteins and glycolipids. In the case of inflammations, tissue-destroying processes and certain tumour diseases, higher concentrations of sialic acids, especially of 5-N-acetylneuraminic acid, and increased activities of so-called sialyl transferases are also found in the blood plasma. The latter incorporate in a physiological manner the sialic acid intracellularly into glycoconjugates; it is a question of glycoprotein enzymes which have a definite specificity for the glycan sequence of the glycoconjugate acceptor into which the sialic acid is incorporated and for the glycosidic binding type in which the incorporated sialic acid is chemically bound. Not only the detection of the sialic acid concentration in the blood and tissues, especially also the sialylation pattern on the cell membrane surface, but also the detection of the sialyl transferase activity and specificity in cells or body fluids is, to an increasing extent, interesting for medical diagnosis.

It is problematical in the case of the detection of such enzymes that they are normally present in extraordinarily low activity so that direct detection methods are difficult. Therefore, according to the state of the art, radioactively-labelled CMP-activated sialic acids are used as substrate in order to determine sialyl transferase-catalysed reactions (cf. Beyer et al., Adv. Enzymol. Relat. Areas Mol. Biol., 52, 23-175 (1981)). Apart from the fact that, in many places, it is difficult to handle radioactive substances, these processes are time-consuming and expensive.

Therefore, there is a need for a simpler labelling substance which is problem-free to handle with which also small amounts of reaction products of the sialyl transferase reaction can be detected certainly, simply and sensitively.

Therefore, in Eur. J. Biochem., 177,583-589 (1988), a process is described of coupling 9-amino-5-N-acetylneuraminic acid with fluoresceinyl isothiocyanate which, according to the process described by Gross and Brossmer, Glycoconjugate J., (1987), Volume 4, 145-176, and Eur. J. Biochem., (1987) 168, 595-602, can be coupled with CMP. The fluorescein-labelled CMP-sialic acid prepared in this way proves, as indicator, to be superior to the known radioactively-labelled CMP-sialic acids. Not only the preparation of the fluoresceinyl-N-acetyl-neuraminic acid but also the subsequent CMP activation proceed, on the basis of the poor reaction and the numerous purification steps, only with a yield of about 5%, referred to the initially used 9-amino-5-N-acetyl-neuraminic acid. Therefore, there is a need to prepare this substance in a simpler way and with higher yields and thus to make it available more economically.

SUMMARY OF THE INVENTION

Surprisingly, it has been found that one can also prepare this compound as well as other hitherto not known CMP-activated, fluorescing sialic acid derivatives in that one first couples 9-amino-5-N-acetylneuraminic acid with CMP as this is described in the literature (cf. Gross et al., Eur. J. Biochem. (1987) 168,595-602). This reaction proceeds with high yield (95%) and also the purification of the end product is comparatively simple. Instead of the preferred 5-acetyl group, another acyl group can also be present. Free 5-amino groups are not suitable since these compounds are not stable.

According to the invention, the so-obtained product can now be coupled with an activated, fluorescing compound, for example with fluorescein isothiocyanate. Surprisingly, this reaction also proceeds with very high yield and comparatively simple purification of the end products, although it was to have been assumed that numerous side reactions would occur due to the large number of possible reactive centres and that a considerable decomposition of the CMP glycosides would occur. Further investigations showed that this process can be employed not only in the case of fluorescein compounds but that practically all other fluorescing compounds which contain a couplable hydroxyl, amino, carboxyl, triazinyl or sulphonic acid group can also be bound by means of suitable activators or coupling compounds to a CMP-activated 9-amino-N-acetylneuraminic acid. Furthermore, it has been shown that the biochemical activity (i.e. the enzyme-kinetic data) of such compounds is even increased when the fluorescing group is bound not via the amino group in the 9-position but rather via an amino group in the 5-position of the N-acylneuraminic acid, whereby, in the latter case, an omega-amino-acyl group, for example β-aminoacetyl, is first condensed as spacer on to the 5-amino group. Although this fluorescent radical then comes spatially close to the glycosidic centre and thus to the important position for the enzymatic catalysis and although until now the N-acetyl group at this position was always regarded as important structural feature for the enzyme-substrate interaction, various sialyl transferases in each case show even a higher affinity (i.e. smaller Michaelis constant) to such compounds in comparison with the corresponding substitution in the 9-position. Equally, it has been shown that the fluorescing group, which is relatively hydrophobic, increases the affinity of most sialyl transferases to the CMP glycoside and thus can be used with advantage as indicators.

Consequently, the process according to the invention consists in reacting a 5-acylamido-9-amino-3,5,9-tridesoxy-β-D-glycero-D-galactononulosonic acid or 5-aminoacylamido-3,5-didesoxy-β-D-glycero-D-galactononulosonic acid of the formula I (in the following briefly designated as 9-amino-5-N-acyl-Neu or 5-aminoacyl-Neu, respectively) of the formula I

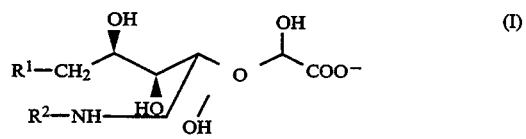

in which $R^1$ represents an amino group and $R^2$ an acyl group or $R^1$ a hydroxyl group or acylamino group and $R^2$ an aminoacyl group, with cytidine phosphate (CTP)

in the presence of a CMP-sialic acid synthase to give CMP-activated sialic acids of the formula II

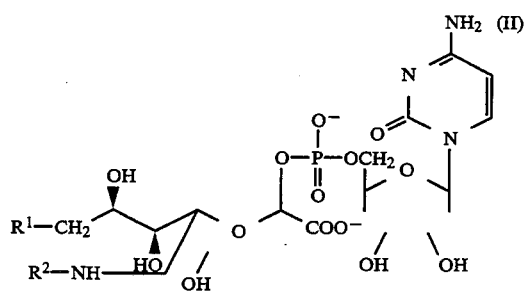

in which $R^1$ and $R^2$ have the above meaning, and reacting this with a fluorescing compound of the formula III Fl—Sp—X    (III)

in which Fl signifies a fluorescing compound, Sp a valency or a coupling spacer group and X an activated carboxyl or thiocarbonyl, triazinyl or sulphonic acid group, to give CMP-activated, fluorescing sialic acids of the formula IV

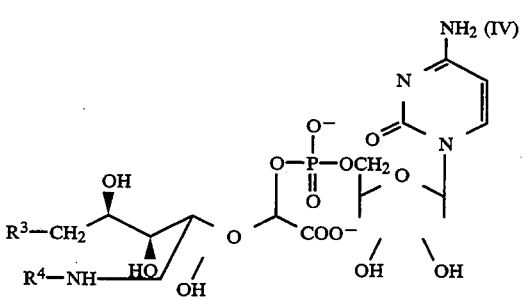

whereby either $R^3$ signifies the group Fl—Sp—X'—NH— and $R^4$ an acyl group or $R^3$ a hydroxyl or acylamino group and $R^4$ the group Fl—Sp—X'—NH-acyl and Fl and Sp in each case have the above meaning and X' signifies a —CO—, —CS—, —SO$_2$— or triazinyl group.

The activated acid group X is a group reacting chemically with an amino group, namely, either to give an amide, e.g. an ester, acid chloride, acid azide, or to give a urea or thiourea, e.g. an isocyanate, isothiocyanate or to give an aminotriazine, e.g. a triazinyl dichloride group. Corresponding reactions are well known for the formation of acid amides. Therefore, equivalent groups are also to be included.

The group Sp is preponderantly a valency since the absorbing or fluorescing compounds frequently contain a couplable group X' directly on the chromophore. However, in other cases, a side chain, especially an alkyl chain with 1–10, preferably 2–6 C-atoms, can also be inserted. By means of a haloalkylcarboxylic acid or haloalkylsulphonic acid, such a group can easily be linked, together with a coupling group X, on to a hydroxyl or amino group of the chromophore.

DESCRIPTION OF PREFERRED EMBODIMENTS

Reaction Principle

Figure 1:
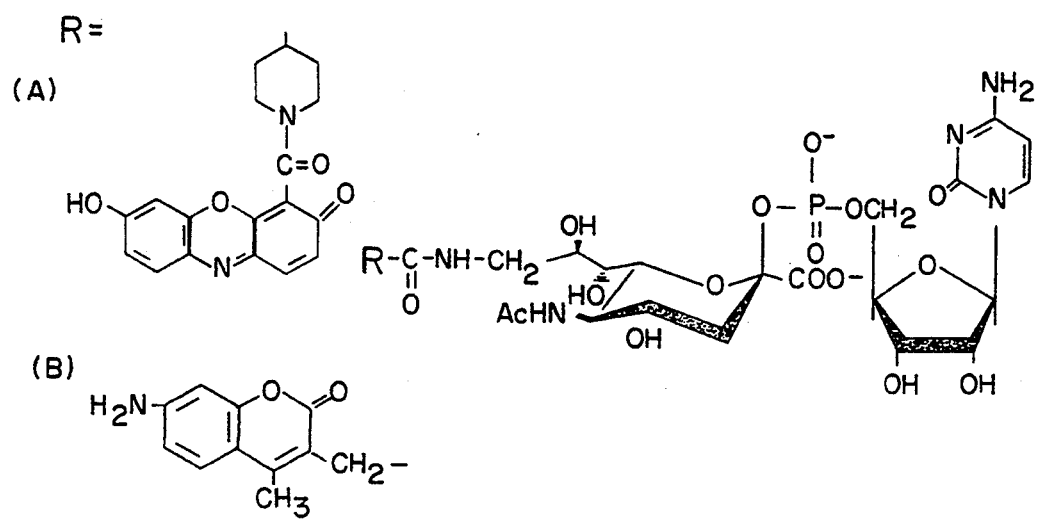
FIGS. 1 through 4 show the structure of CMP-activated, fluorescing neuraminic acid analogues according to the invention.

The starting substance for the synthesis of CMP-activated, fluorescing neuraminic acid analogues is CMP-9-amino-N-acetylneuraminic acid or CMP-5-amino-acetamidoneuraminic acid; furthermore, there are suitable all 5-substituted analogues with longer chains (e.g. N-($\epsilon$-aminopropyl)-neuraminic acid) on C-5 analogous to the 5-aminoacetyl group.

The reaction takes place by coupling of the starting material via the primary amino group on position C-9 or C-5 with various reactive fluorescing or absorbing substances which react easily with an amino function. Activated substituents can be present as isothiocyanates, isocyanates, as N-hydroxysuccinimide esters, p-nitrophenyl esters, sulphonic acid chlorides, as triazine chlorides or as acid azides.

The reaction takes place in partly aqueous medium in the neutral or alkaline pH range (7.5–10; the reaction takes place best at pH 8.5–9) at 20° C. or better at 37° C. with the addition of organic solvents for the solubilisation of the reactive substance (e.g. 30%–80% methanol, DMF dimethylformamide, DMSO dimethyl sulfoxide, acetone or acetonitrile and the like). The CMP-glycoside starting material and the CMP-NeuAc analogue formed remain stable in the mentioned pH range (less than 5% decomposition). The excess of activated fluorescent agent can, in the case of isothiocyanates, amount to only 2 fold in order to achieve more than 90% reacted CMP glycoside; in the case of N-hydroxysuccinimide esters, it better lies at 3–5 fold in order to achieve the same reaction; in principle, a 10 fold excess is favourable for the shortening of the reaction time (in the case of isothiocyanates usually 10–15 min. at 37° C., in the case of N-hydroxysuccinimide esters up to 20–30 min.). In the case of triazinyl dichloride as reactive group, a higher excess is recommended (6 to 15 fold), the reaction time up to the complete reaction (90%) amounts to at least 15–20 h. at 37° C.

In all cases, a reaction to the fluorescing or absorbing CMP-NeuAc analogue of 90% or more is achieved. Subsequently, the synthesised fluorescing or absorbing CMP-NeuAc analogue is purified via preparative HPLC (cf. Gross and Brossner, Eur. J. Biochem., 177, 583–89). ("Spherisorb NH$_2$" (Zinsser), Aminoprepyl (Serva), "Lichroprep NH$_2$" (E. Merck) as stationary phase and 15 mM KH$_2$PO$_4$ in water/50–70% acetonitrile as mobile phase).

Advantages of the New Method

For the first time, new CMP-NeuAc analogues were prepared chemically with this method directly from a CMP glycoside. The advantage of the here-shown method is the direct coupling of the reactive substituent with an amino group of a CMP glycoside; there is thereby unnecessary a laborious and expensive chemical synthesis first of the corresponding free NeuAc analogue, the purification thereof and the subsequent enzymatic activation of each free NeuAc analogue with CMP-sialic acid synthase with subsequent further purification. After the chemical synthesis according to the invention, only a simple purification procedure has to be carried out. Furthermore, the yields in the case of this enzymatic reaction of free NeuAc analogues with large fluorescent substituents on C-9 or C-5 is substantially lower (about 15%), as was shown by the enzymatic synthesis of CMP-9-fluoresceinyl-NeuAc. On the other hand, CMP-9-amino-NeuAc can be prepared with optimum yield of 95% via CMP-NeuAc synthase reaction. The coupling reaction of fluorescent substituents to CMP-9-amino-NeuAc also proceeds with reaction rates of 90% and more so that the new method guarantees optimum yields. The method is thus economic, simple and time-saving and makes it possible to prepare a plurality of CMP-NeuAc analogues due to the multiplicity of the possible activated substituents. The known instability of the CMP glycosides thereby represents no ground of hindrance since especially CMP-9-amino-NeuAc is surprisingly stable in the mentioned pH range (pH 7.5–9.5).

below 6%, CTP was smaller than 0.1% and inorganic phosphate was below 50%.

The new substrates according to the invention can be used for the following analytical methods:
1. activity determination of sialyl transferase
2. acceptor specificity determination and determination of the kinetic acceptor data of sialyl transferase
3. fluorescence labelling of cell surfaces
4. labelling of glycoproteins and gangliosides.

Characteristic of some fluorescing CMP glycosides
All fluorescent CMP-NeuAc analogues were prepared according to the described process

| fluorescent CMP-glycosides | absorption maximum* (between 230-700 nm) | absorption maximum*** (literature) | retention time in the HPLC-system* (peak maximum) | absorption coefficient $\epsilon$ (275 nm) in the HPLC-system (referred to (275 nm) of CMP) |
|---|---|---|---|---|
| CMP-9-fluoresceinyl-amino-NeuAc (CMP-9-FITC-NeuAc) | 492 nm | 495 nm | 24.5 min | 3.2 ± 0.2 |
| CMP-5-fluorescienyl-aminoacetyl-Neu (CMP-5-FITC-Neu) | 493 nm | 495 nm | 44.5 min | 3.2 ± 0.2 |
| CMP-9-N-(fluoresceinyl-aninochlorotriazinyl)-amino-NeuAc (CMP-9-DTAF-NeuAc) | 1. Max 233 nm 2. Max 493 nm | 492 nm | 21.5 min | 4.25 ± 0.35 |
| CMP-9-tetramethyl-rhodaminylamino-NeuAc (CMP-9-TRITC-NeuAc) | 552 nm | 554 nm | 28.1 min | 2.4 ± 0.3 |
| CMP-9-resorufinyl-amino-NeuAc (CMP-9-RESOS-NeuAc) | 577 nm | 575.6 nm | 47.5 min | 1.8 ± 0.15 |
| CMP-9-(7-amino-4-methyl)-caumarinyl-acetamido-NeuAc (CMP-9-AMCA-NeuAc) | 339 nm | 345 nm | 17.5 min | 1.2 ± 0.15 |
| reference CMP | 273 nm | 273 nm | 8.5 min | 1.0 |

*measured in 50 mM Na phosphate buffer pH 7.0
**HPLC-system as described; Gross et al, Eur. J. Biochem. (1987) 168, 595–602 flow rate 3 ml/min; detection at 275 nm; 40% 15 mM KH$_2$PO$_4$/60% acetonitrile
***absorption maximun of the activated fluorescence substituents (FITC, TRITC, DTAF, RESOS, AMCA) according to catalogue/literature Characteristic of the prepared CMP-NeuAc analogues:

The new fluorescent or absorbing CMP glycosides were, after purification, characterised with various methods (see following Table).

1. The retention time in the analytical HPLC system (275 nm) differs from the CMP-9-amino-NeuAc or CMP-5-aminoacetamido-Neu, the absorption coefficient ($\epsilon$) of the new CMP glycosides in the HPLC system at 275 nm lay above 1.0 (referred to $\epsilon_{275\ nm}$ of CMP).

2. By means of mild acid hydrolysis (1N HCl, 45 min. at RT), the new CMP glycosides were completely decomposed to CMP and subsequently determined by analytical HPLC (275 nm). In the analytical HPLC system, at 200 nm there appeared, after acid hydrolysis, the peak of the liberated, fluorescent or absorbing NeuAc analogue.

3. The absorption spectrum and the fluorescence spectrum of the new CMP glycosides was measured; the absorption or fluorescence maxima of the fluorescent or absorbing substituents could be found again practically at identical wavelength in the new CMP glycoside (see following Table).

4. The contamination with free CMP or free NeuAc derivative lay, in the case of the new CMP glycosides, I. Measurement of the sialyl transferase activity.

The test is based upon the incorporation of the fluorescing neuraminic acid derivative from the corresponding CMP glycoside by means of a sialyl transferase into an acceptor, for example a glycoprotein or ganglioside, separation of the substituted and unsubstituted acceptor molecules from the excess of the reagents by gel filtration or precipitating out and measurement of the acceptor-bound fluorescence by means of a corresponding spectrometric process. This method is suitable for the determination of all previously known sialyl transferases in spite of differing binding ($\alpha$2,3-; $\alpha$2,6-) and acceptor specificity (Gal$\beta$1; GlcNAc-; Gal$\beta$1,4(3)Glc-NAc-; Gal$\beta$i,3GalNAc-; GalNAc-) since plainly, in general, the substrate specificity with regard to the position C9 or C5 of the CMP-activated neuraminic acids is not very marked. As stated above, C5-substituted neuraminic acids and neuraminic acids substituted by hydrophobic substituents prove to be substrates with especially high affinity.

For a simple test, normally 30 $\mu$l of reaction solution or possibly only up to 10 $\mu$l of reaction solution are needed. This enzymatic reaction is carried out, for example, in a buffer with pH 6 or 6.5 (depending upon the pH optimum of the sialyl transferase), whereby 0.1–10.0 mg/ml of acceptor [(asialo)-glycoprotein or ganglioside], corresponding to 690–1,875 $\mu$m of galactose or N-acetylgalactosamine acceptor positions, and 10–100 mM of the particular CMP-activated fluorescent N-acetylneuraminic acid reagents are added thereto. The reaction solution is usually maintained for 10 min. to 45 min. at 37° C. and subsequently separated in a Sephadex G50 column (0.4×12 cm) with 0.1M tris buffer pH 8.6 [in the case of ganglioside acceptors, the buffer additionally contains 100 mM NaCl and 0.3% of detergent (e.g. Triton X-100)]. The extent of the reaction is quantified via a fluorescence measurement of the macromolecular-bound fluorescent neuraminic acid but can possibly also be determined via a measurement of the non-reacted fluorescent CMP glycoside. In contradistinction to radiometric tests for sialyl transferase activity, substantially smaller concentrations of the fluorescent CMP glycoside (5–15 fold smaller) suffice in order to saturate the enzyme with the CMP glycoside and the small volumes needed for the fluorescence measurement make possible small reaction solutions (to min. 10 µl), which, in all, makes the method very economical. Nevertheless, the measurement sensitivity of the fluorometric test is difficult to achieve in a radiometric test (requires very highly specific radio-labelling).

The test is suitable in this form also especially for the measurement of the small sialyl transferase activities in culture cell lines, operation or biopsy material and in body fluids, especially in blood plasma or serum.

As alternative to the gel filtration, in the case of glycoprotein acceptors, a precipitation for the separation from the donor is possible; for this purpose, an assay is precipitated as above with 1 ml 1% PWS in 0.5N HCl at 4° C. and 20 min. The sediment is washed twice with ethanol/0.1M tris pH 7.5 (9/1) and dissolved in a suitable volume of 1N NaOH (PWS=phosphotungstic acid).

II. Sialyl transferases of different origin display, in part, considerable differences in their acceptor substrate specificity. With use of the indicators according to the invention, there can, therefore, be built up a simple differentiation reaction to carry out the above test under standardised conditions in each case with different acceptors (i.e. glycoprotein, glycolipid or oligosaccharide acceptors with different glycan sequences) and to compare the particular activity found. The test also makes possible the production of enzyme-kinetic data (Michaelis constant, $V_{max}$) for the acceptor in question. In plasma or serum, the test makes possible for the first time a differentiation of two sialyl transferases, one with specificity for the N-bound, terminal glycan sequence Gal$\beta$1,4GlcNAc, another for O-bound GalNAc residues.

III. Furthermore, it is possible to label the sialic acid acceptors on cell membranes in a simple way with the indicators according to the invention in that one allows an appropriate reaction solution of the CMP-activated fluorescent sialic acid to act in the presence of sialic transferase, to wash out the excess of the indicator and to determine surface properties of particular cells to be investigated by the extent of the fluorescence of the isolated cells. Furthermore, in this way, the cells can be selectively fluorescent-labelled in the glycan part without a chemical heat treatment. The measurement of the surface-bound fluorescence takes place very simply in a flow-through cytometer but can also be observed under the fluorescence microscope.

IV. Furthermore, the compounds according to the invention prove to be advantageous when certain proteins which are especially sensitive in their spatial structure are to be fluorescence-labelled in order to be able to monitor them in the case of use in a biological system on the basis of the fluorescence. Such a labelling can be carried out enzymatically relatively gently and completely, leaves the actual amino acid sequence of the protein unmodified, takes place selectively in particular glycan sequences and makes it possible easily again to separate off the excess indicator substance. The process procedure is, in principle, the same as described under I.

Preferred Fluorescent or Absorbing CMP Glycosides

CMP-9-TRITC-NeuAc: this substance is transmitted to glycoproteins practically only by Gal$\beta$1,4GalNAc $\alpha$2,6-sialyl transferases, could thus serve for the differentiation; furthermore, different excitation and emission (red fluorescent).

CMP-9-DTAF-NeuAc: strongly hydrophobic, better kinetic data for different sialyl transferases, especially for Gal$\beta$1,3GalNAc $\alpha$2,3-sialyl transferase $V_{max}$/kin is 6.5 times higher than for CMP fluoresceinyl-NeuAc CMP-9-RESOS-NeuAc: very good absorption in the visible range; in the case of fluorescence, different emission also excitation than FITC; fluorescence also in the acidic pH range in contradistinction to FITC.

CMP-9-AMCA-NeuAc: excitation in the UV range, smaller "inner quench" by 100 nm distance between excitation and emission; fluorescence not pH-dependent in a wider range.

CMP-9-DAB-NeuAc: excitation in the UV range; high absorption in the UV range, therefore good suitability for an absorption assay for UV flowthrough spectrophotometers.

CMP-5-FITC-Neu: Favourable emission and excitation frequencies in the case of high fluorescence yield. Kinetic data in the case of sialyl transferases of the most different acceptor specificity always superior to those of CMP-9-fluoresceinyl-NeuAc ($V_{max}$/kin.: 2.8–20 times higher).

Figure 2:
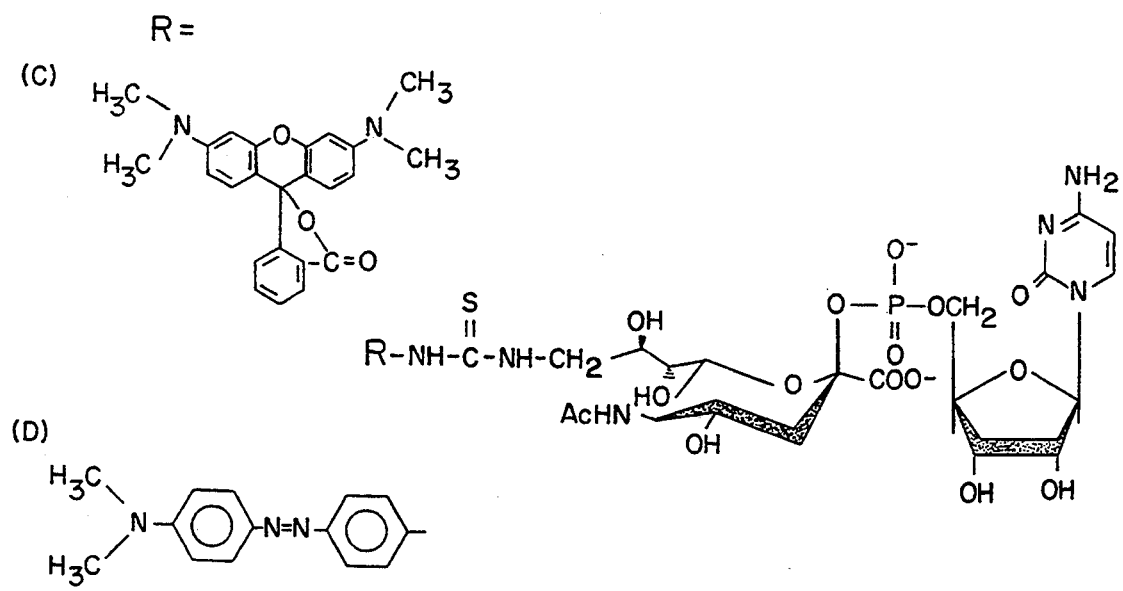

CMP-sialic acid derivatives selected from the group:
in each case:
trivial name
exact chemical nomenclature
abbreviated trivial name CMP-9-tetramethylrhodaminylamino-NeuAc
CMP-[5-acetamido-9-(3-tetramethylrhodaminylthioureido)-3,5,9-tridesoxy]-$\beta$-D-glycero-D-galactononulosonic acid (CMP-9-TRITC-NeuAc) see FIG. 2: Structure 2, radical C CMP-9-rhodaminylamino-NeuAc
CMP-[5-acetamido-9-(3-rhodaminylthioureido)-3,5,9-tridesoxy]-$\beta$-D-glycero-D-galactononulosonic acid (-.-)

CMP-9-eosinylamino-NeuAc
CMP-[5-acetamido-9-(3-eosinylthioureido)-3,5,9-tridesoxy]-$\beta$-D-glycero-D-galactononulosonic acid (-.-)

CMP-9-(4-N,N'-dimethylaminoazobenzo-4)-amino-NeuAc
CMP-[5-acetamido-9-(4-N,N'-dimethylaminoazobenzo-4'-thioureido)-3,5,9-trideoxy]-$\beta$-D-glycero-D-galactononulosonic acid
(CMP-9-DAB-NeuAc)
See FIG. 2: Structure 2, radical D CMP-9-fluoresceinyl-(5,6)-carboxamido-NeuAc
CMP-5-acetamido-[9-fluoresceinyl-(5,6)-carboxamido]-3,5,9-tridesoxy-$\beta$-D-glycero-D-galactononulosonic acid
(CMP-9-Fl OUS-NeuAc)

Figure 3:
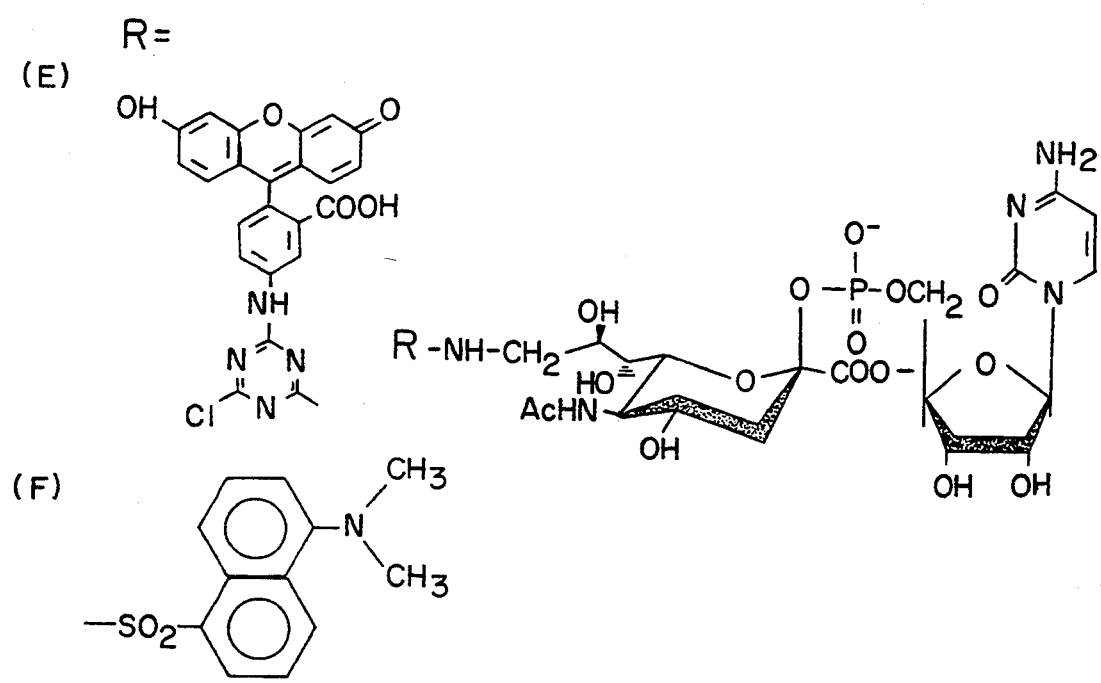
Figure 4:
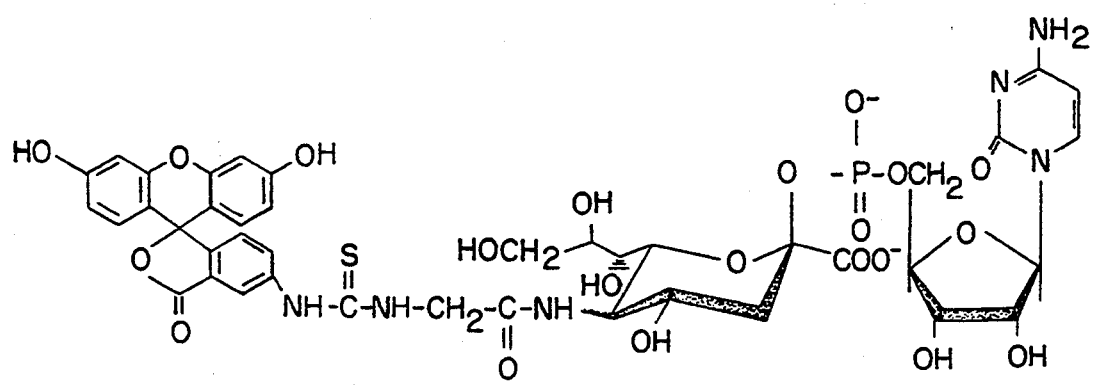

CMP-9-rhodaminyl-(5,6)-carboxamido-NeuAc
CMP-5-acetamido-[9-rhodaminyl-(5,6)-carboxamido]-3,5,9-tridesoxy[-$\beta$-D-glycero-D-galactononulosonic acid (CMP-9-RHODOS-NeuAc)
CMP-9-resorufinylamino-NeuAc
CMP-5-acetamido-9-[(N-resorufin-4-carbonyl)-piperidine-4-carboxamido]-3,5,9-tridesoxy-β-D-glycero-D-galactononulosonic acid
(CMP-9-RESOS-NeuAc)
See FIG. 1: Structure 1, radical A
CMP-9-(7-amino-4-methylcumarinylacetamido)-NeuAc CMP-5-acetamido-9-(7-amino-4-methylcoumarinylacetamido)-3,5,9-tridesoxy-β-D-glycero-D-galactononulosonic acid
(CMP-9-AMCA-NeuAc)
See FIG. 1: Structure 1, radical B
CMP-9-N-(fluoresceinylaminochlorotriazinyl)-amino-NeuAc
CMP-5-acetamido-9-fluoresceinylaminochlorotriazinyl-amino-3,5,9-tridesoxy-β-D-glycero-D-galactononulosonic acid
(CMP-9-DTAF-NeuAc)
See FIG. 3: Structure 3, radical E
CMP-9-dansylamino-NeuAc
CMP-5-acetamido-9-(dansylamino)-3,5,9-tridesoxy-β-D-glycero-D-galactononulosonic acid
See FIG. 3: Structure 3, radical F
CMP-9-(Texas-Red)-amino-NeuAc
CMP-5-acetamido-9-N-(Texas-Red)-amino-3,5,9-tridesoxy-β-D-glycero-D-galactononulosonic acid
CMP-5-fluoresceinylaminoacetyl-Neu
CMP-3,5-didesoxy-5-(fluoresceinylthioureido)-acetamido-β-D-glycero-D-galactononulosonic acid
(CMP-5-FITC-NeuAc)
See FIG. 4: Structure 4, (fluoresceinyl isomer I)
CMP-5-tetramethylrhodaminylaminoacetyl-Neu
CMP-3,5-didesoxy-5-(tetramethylrhodaminylthioureido)-acetamido-β-D-glycero-D-galactononulosonic acid
(CMP-5-TRITC-Neu)
CMP-5-rhodaminylaminoacetyl-Neu
CMP-3,5-didesoxy-5-(rhodaminylthioureido)-acetamido-β-D-glycero-D-galactononulosonic acid (-.-)
CMP-5-eosinylaminoacetyl-Neu
CMP-3,5-didesoxy-5-(eosinylthioureido)-acetamido-β-D-glycero-D-galactononulosonic acid (-.-)
CMP-5-xanthenerhodaminylaminoacetyl-Neu
CMP-3,5-didesoxy-5-(xanthenerhodaminylthioureido)-acetamido-β-D-glycero-D-galactononulosonic acid
(CMP-5-XRITC-Neu)
CMP-5-(4-N,N'-dimethylaminoazobenzo-4')-aminoacetyl-Neu
CMP-3,5-didesoxy-5-(4-N,N'-dimethylaminoazobenzo-4'-thioureido)-acetamido-β-D-glycero-D-galactononulosonic acid
(CMP-5-DAB-Neu)
CMP-5-fluoresceinyl-(5,6)-carboxamidoacetyl-Neu
CMP-3,5-didesoxy-5-fluoresceinyl-(5,6)-carboxamido-acetamido-β-D-glycero-D-galactononulosonic acid
(CMP-5-FLUOS-Neu)
CMP-5-rhodaminyl-(5,6)-carboxamidoacetyl-Neu
CMP-3,5-didesoxy-5-rhodaminyl-(5,6)-carboxyamido-acetamido-β-D-glycero-D-galactononulosonic acid
(CMP-5-RHODOS-Neu)
CMP-5-resorufinylacetyl-Neu
CMP-3,5-didesoxy-5-N-(resorufin-4-carbonyl)-piperidine-4-carboxamido)-acetamido-β-D-glycero-D-galactononulosonic acid
(CMP-5-RESOS-Neu)
CMP-5-(7-amino-4-methylcumarinylacetamido)-acetyl-Neu
CMP-3,5-didesoxy-5-N-(7-amino-4-methylcoumarinyl-acetamido)-acetamido-β-D-glycero-D-galactononulosonic acid
(CMP-5-AMCA-Neu)
CMP-5-fluoresceinylaminochlorotriazinylaminoacetyl-Neu
CMP-3,5-didesoxy-5-N-(fluoresceinylaminochlorotriazinyl)-aminoacetamido-β-D-glycero-D-galactononulosonic acid
(CMP-5-DTAF-Neu)
CMP-5-dansylaminoacetyl-Neu
CMP-5-dansylaminoacetamido-β-D-glycero-D-galactononulosonic acid
CMP-5-(Texas-red)-aminoacetyl-Neu
CMP-3,5-didesoxy-5-N-(Texas-red)-aminoacetamido-β-D-glycero-D-galactononulosonic acid.

Preparation in Detail of Fluorogenic CMP Glycosides a) Synthesis of CMP-9-fluoresceinylamino-NeuAc Fluoresceinyl isothiocyanate (isomer I or II is dissolved in methanol of DMF (1–4 mg=about 2.5–10 μmol; in 200 μl), then 1.25 μmol CMP-9-amino-NeuAc, dissolved in 200 μl of water added thereto (2 mol fluoresceinyl isothiocyanate per mol of CMP-9-amino-NeuAc are sufficient); then 20 μl of a buffer solution pH 9–9.5 (e.g. 0.5M NaNCO$_3$/Na$_2$CO$_3$) are added thereto so that pH 8.5–9 is achieved. The reaction of the amino group on C-9 of the NeuAc part of the CMP glycoside with the fluoresceinyl isothiocyanate is complete after at most 15 min. (greater than 90%). The reaction can be observed via analytical HPLC. The retention time of CMP-9-amino-NeuAc is substantially smaller than that of the fluorescent CMP glycoside formed. The purification of the CMP-9-fluoresceinyl-NeuAc obtained takes place via preparative HPLC and ethanol precipitation as described (Gross and Brossner, (1988), Eur. J. Biochem., 177, 583–89).

b) Synthesis of CMP-9-resorufinylamino-NeuAc.

0.5 mg N-(resorufin-4-carbonyl)-piperidine-4-carboxylic acid N'-hydroxysuccinimide ester (RESOS 0.5 mg±about 1.1 μmol) is dissolved in 100 μl DMF; then 20 to 80 μl of an aqueous solution of CMP-9-amino-NeuAc (0.5 μmol) are added thereto and 20 μl of buffer pH 9–9.5 (see synthesis of CMP-9-fluoresceinyl-NeuAc). The pH of the reaction solution should be 8.5–9, the formation of CMP-9-resorufinyl-NeuAc (yield over 90%) is complete after 20 min. (analyt. HPLC as above). The purification takes place as in the case of CMP-9-fluoresceinyl-NeuAc.

c) Synthesis of CMP-5-fluoresceinylaminoacetyl-Neu.

The synthesis takes place exactly as described above for CMP-9-fluoresceinyl-NeuAc but with CMP-5-aminoacetamido-Neu as starting material (2 mol fluoresceinyl isothiocyanate/mol CMP-5-aminoacetamido-Neu). The coupling is achieved with over 90% yield in 15 min. (analyt. HPLC as above). The purification is carried out as in the case of CMP-9-fluoresceinyl-NeuAc.

d) Synthesis of CMP-9-N-(fluoresceinylaminochlorotriazinyl)-amino-NeuAc 2.0 mg (=3.75 μmol) dichlorotriazinylamino-fluorescein (DTAF) was dissolved in 100 μl DMF; then 20–50 μl of an aqueous solution of CMP-9-amino- NeuAc (max. 0.5 μmol) and 20 μl buffer pH 9–9.5 (as synthesis of CMP-9-fluorosceinyl-NeuAc) added thereto (7.5–19 mol DTAF/mol CMP-9-amino-NeuAc). After 3 h., about 75% of the CMP-9-amino-NeuAc have reacted, after 15 h. more than 90% (analyt. HPLC as above). The purification takes place as described in the case of CMP-9-fluorosceinyl-NeuAc.

e) Synthesis of CMP-9-(7-amino-4-methylcoumarinyl-acetamido)-NeuAc 0.3 mg AMCA-N-hydroxysuccinimide ester (about 1 μmol) was dissolved in 130 μl DMF; then 70 μl of an aqueous solution of CMP-9-amino-NeuAc (about 0.5 μmol) and 30 μl of buffer pH 9–9.5 (as synthesis of CMP-9-fluorosceinyl-NeuAc) added thereto (2 mol AMCA/mol CMP-9-amino-NeuAc). After 20 min., about 90–95% of the CMP-9-amino-NeuAc are reacted (analyt. HPLC as above). The purification takes place as described in the case of CMP-9-fluorosceinyl-NeuAc.

We claim:

1. Process for the preparation of cytidine-5'-monophoshate-activated (CMP-activated) fluorescence indicator-labelled sialic acids of the formula IV

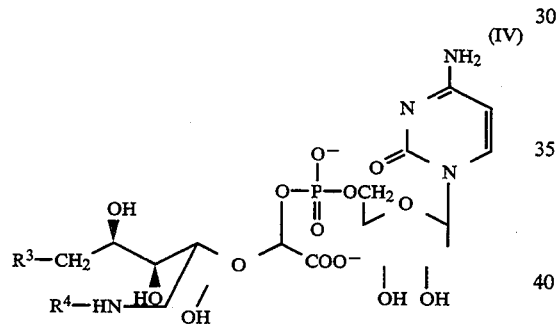

wherein either $R^3$ signifies the group Fl—Sp—X'—NH— and $R^4$ an acyl group or $R^3$ a hydroxyl or acylamino group and $R^4$ the group Fl—Sp—X'—NH-acyl, Fl signifies a fluorescing group, Sp a valency or a coupling spacer group and X' a —CO—, —CS—, —SO$_2$— or triazinyl group, comprising reacting a 9-amino-5-N-acyl- or 5-aminoacyl-neuraminic acid of the formula I

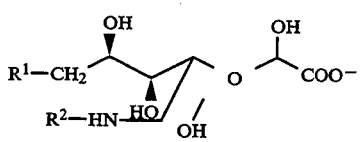

in which $R^1$ represents an amino group and $R^2$ an acyl group or $R^1$ a hydroxyl or acylamino group and $R^2$ an aminoacyl group, with cytidine triphosphate (CTP) in the presence of the enzyme CMP-sialic acid synthase (E.C. 2.7.7.43) to give CMP-activated sialic acids of the formula II

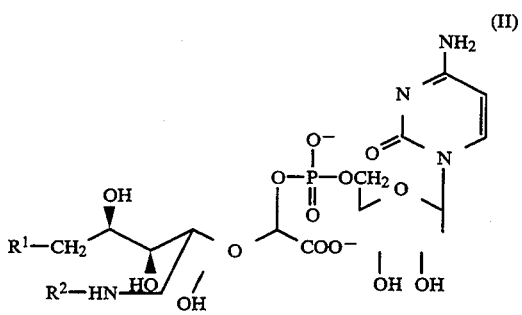

in which $R^1$ and $R^2$ have the above meaning, and reacting the CMP-activated sialic acids of formula II with a fluorescing compound of the formula III

 Fl—Sp—X (III)

in which Fl signifies a fluorescing group, Sp a valency or a coupling spacer group and X an activated carboxyl, thiocarbinyl, triazinyl or sulphonic acid group, to give CMP-activated, fluorescing sialic acids of the formula IV

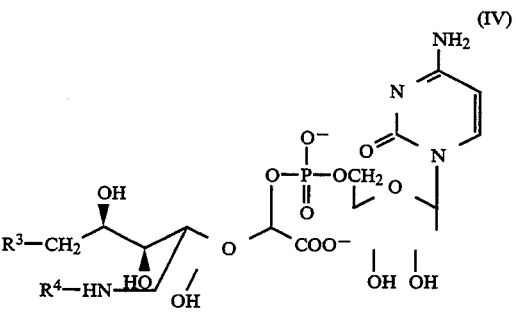

wherein $R^3$ and $R^4$ have the above meaning.

2. Process according to claim 1, wherein a fluorescent indicator of the formula V

 Fl—R$^5$ (V)

in which $R^5$ signifies an amino, hydroxyl, carboxyl, triazinyl or sulphonyl group and Fl a fluorescing group, is coupled with an activated acid group X to give the fluorescing compound III

 Fl—Sp—X (III)

which is thereafter reacted with the 9- or 5-amino group of the sialic acid of the formula II.

3. CMP-activated fluorescence indicator-labelled sialic acid of the formula IV'

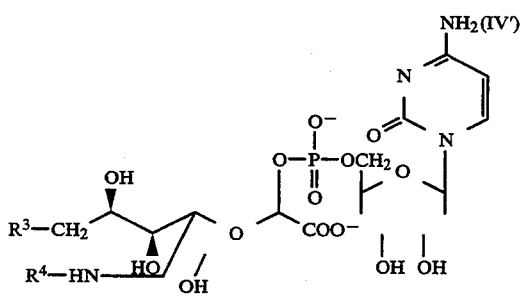

wherein either $R^3$ is the group Fl—Sp—X'—NH— and $R^4$ is an acyl group or, alternatively, $R^3$ is a hydroxyl group or acylamino group and $R^4$ is the group Fl—Sp—X'—NH-acyl in which Fl is a fluorescing group and Sp is a valency or a coupling spacer group and X' signifies a —CO—, —CS— or —SO$_2$— or triazinyl group, wherein $R^3$ is not a fluoresceinyl group.

4. The CMP-activated sialic acid according to claim 3, wherein the group —Sp— is an alkyl group with 1-10 C-atoms.

5. The CMP-activated sialic acid according to claim 3, further comprising a fluorescing group Fl—Sp—X' attached to the 5-position of an acylamino group.

6. The CMP-activated sialic acid according to claim 3, wherein the group X' is a ureido or thioureido group.

7. The CMP-activated sialic acid according to claim 3, wherein the group X' is an N-hydroxy-succinimide group.

8. The CMP-activated sialic acid according to claim 4, further comprising the fluorescing group Fl—Sp—X' attached to the 5-position of an acylamino group which represents a fluoresceinyl-thioureidoacetyl group.

9. The CMP-activated sialic acid according to claim 4, wherein the group X' is a ureido or thioureido group.

10. The CMP-activated sialic acid according to claim 5, wherein the group X' is a ureido or thioureido group.

11. The CMP-activated sialic acid according to claim 4, wherein the group X' is an N-hydroxysuccinimide group.

12. The CMP-activated sialic acid according to claim 5, wherein the group X' is an N-hydroxysuccinimide group.

13. The CMP-activated sialic acid according to claim 4, wherein the group —Sp— is an alkyl group with 2-6 C-atoms.

14. The CMP-activated sialic acid according to claim 5, wherein the fluorescing group Fl—Sp—X' represents a fluoresceinylthioureidoacetyl group.

15. CMP-sialic acid derivatives selected from the group consisting of
CMP-9-tetramethylrhodaminylamino-NeuAc
CMP-9-rhodaminylamino-NeuAc
CMP-9-eosinylamino-NeuAc
CMP-9-xanthenerhodaminyl-NeuAc
CMP-9-(4-N,N'-dimethylaminoazobenzo-4)-amino-NeuAc
CMP-9-fluoreseinyl-(5,6)-carboxamido-NeuAc
CMP-9-rhodaminyl-(5,6)-carboxamido-NeuAc
CMP-9-resorufinylamino-NeuAc
CMP-9-(7-amino-4-methylcoumarinylacetamido)-NeuAc
CMP-9-N-(fluoresceinylaminochlorotriazinyl)-amino-NeuAc
CMP-9-dansylamino-NeuAc
CMP-9-(Texas-red)-amino-NeuAc
CMP-5-fluoresceinylaminoacetyl-Neu
CMP-5-tetramethylrhodaminylaminoacetyl-Neu
CMP-5-rhodaminylaminoacetyl-Neu
CMP-5-eosinylaminoacetyl-Neu
CMP-5-xanthenerhodaminylaminoacetyl-Neu
CMP-5-(4-N,N'-dimethylaminoazobenzo-4')-aminoacetyl-Neu
CMP-5-fluoresceinyl-(5,6)-carboxamidoacetyl-Neu
CMP-5-rhodaminyl-(5,6)-carboxamidoacetyl-Neu
CMP-5-resorufinylacetyl-Neu
CMP-5-(7-amino-4-methylcoumarinylacetamido)-acetyl-Neu
CMP-5-fluoresceinylaminochlorotriazinylaminoacetyl-Neu
CMP-5-dansylaminoacetyl-Neu and
CMP-5-(Texas-red)-aminoacetyl-Neu.

16. A method of measuring sialyl transferase activity, comprising the steps of:

incorporating into an acceptor molecule, by means of a sialyl transferase, a CMP-activated fluorescence indicator-labelled sialic acid of the formula IV

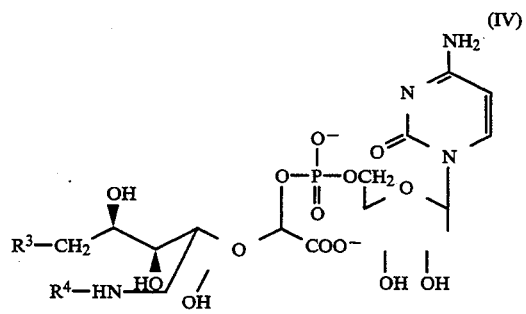

wherein either $R^3$ signifies the group Fl—Sp—X'—NH— and $R^4$ an acyl group or $R^3$ a hydroxyl or acylamino group and $R^4$ the group Fl—Sp—X$^1$—NH-acyl, Fl signifies a fluorescing group, Sp a valency or a coupling spacer group and X' a —CO—, —CS—, —SO$_2$— or triazinyl group; and measuring acceptor-bound fluorescence.

17. A method as claimed in claim 16, wherein said acceptor molecule is a ganglioside or glycoprotein.

18. A method as claimed in claim 16, further comprising reacting a fluorescing group Fl—Sp—X' with a 5-aminoacetyl neuraminic acid.

19. A method of measuring differences in acceptor substrate specificity of different sialyl transferases, comprising the steps of:

incorporating, by means of a first sialyl transferase, a cytidine-5'-monophosphate-activated (CMP-activated) fluorescence indicator-labelled sialic acid of the formula IV,

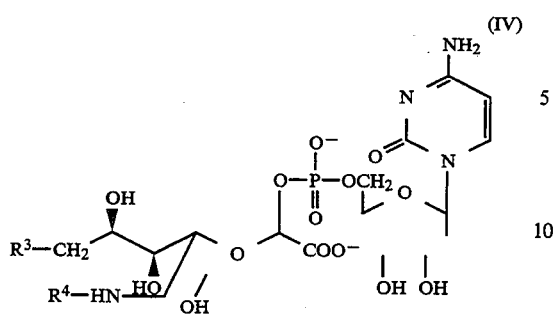

(IV)

wherein either $R^3$ signifies the group Fl—Sp—X'—NH— and $R^4$ an acyl group or $R^3$ a hydroxyl or acylamino group and $R^4$ the group Fl—Sp—X'—NH-acyl, Fl signifies a fluorescing group, sp a valency or a coupling spacer group and X' a —CO—, —CS—, —$SO_2$— or triazinyl group, into a first acceptor molecule;

incorporating, by means of a second sialyl transferase, a CMP-activated fluorescence indicator-labelled sialic acid of the formula IV into a second acceptor molecule; and measuring and comparing the level of fluorescence of said first and second acceptor-bound sialic acids.

20. A method as claimed in claim 19, further comprising reacting a fluorescing group Fl—Sp—X' with a 5-aminoacetyl neuraminic acid.

21. A method of labelling a cell surface, comprising the steps of:

bringing a solution of cells into contact with a cytidine-5'-monophosphate-activated (CMP-activated) fluorescence indicator-labelled sialic acid of the formula IV,

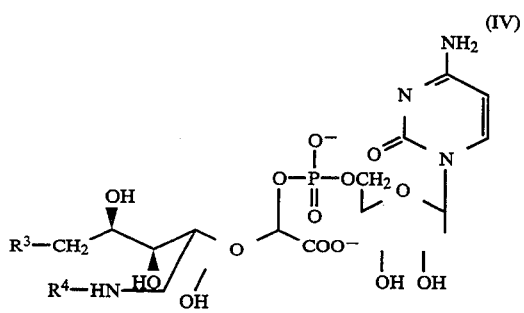

(IV)

wherein either $R^3$ signifies the group Fl—Sp—X'—NH— and $R^4$ an acyl group or $R^3$ a hydroxyl or acylamino group and $R^4$ the group Fl—Sp—X'—NH-acyl, Fl signifies a fluorescing group, Sp a valency or a coupling spacer group and X' a —CO—, —CS—, —$SO_2$— or triazinyl group, in the presence of sialic transferase;

washing away excess indicator-labelled sialic acid; and measuring surface-bound fluorescence.

22. A method as claimed in claim 21, further comprising reacting a fluorescing group Fl—Sp—X' with a 5-aminoacetyl neuraminic acid.

* * * * *